(12) United States Patent
Kim

(10) Patent No.: US 11,013,458 B2
(45) Date of Patent: May 25, 2021

(54) BREATH ANALYSIS SYSTEM USING GAS IMAGE DETECTION METHOD

(71) Applicant: AJOU UNIVERSITY INDUSTRY-ACADEMIC COOPERATION FOUNDATION, Suwon-si (KR)

(72) Inventor: Hyun Jun Kim, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 96 days.

(21) Appl. No.: 16/345,230

(22) PCT Filed: Sep. 29, 2017

(86) PCT No.: PCT/KR2017/011018
§ 371 (c)(1),
(2) Date: Apr. 25, 2019

(87) PCT Pub. No.: WO2018/080048
PCT Pub. Date: May 3, 2018

(65) Prior Publication Data
US 2019/0274621 A1 Sep. 12, 2019

(30) Foreign Application Priority Data
Oct. 28, 2016 (KR) .......................... 10-2016-0141615

(51) Int. Cl.
*A61B 5/00* (2006.01)
*A61B 5/01* (2006.01)
(Continued)

(52) U.S. Cl.
CPC .............. *A61B 5/4818* (2013.01); *A61B 5/00* (2013.01); *A61B 5/0075* (2013.01); *A61B 5/01* (2013.01);
(Continued)

(58) Field of Classification Search
CPC ....... A61B 5/4818; A61B 5/08; A61B 5/0075; A61B 5/02055; A61B 5/0476;
(Continued)

(56) References Cited

U.S. PATENT DOCUMENTS

2003/0135097 A1   7/2003   Wiederhold et al.
2006/0264762 A1*  11/2006  Starr ................... A61M 16/104
                                                      600/483
(Continued)

FOREIGN PATENT DOCUMENTS

JP   2007-105147 A   4/2007
JP   2013-070997 A   4/2013
(Continued)

OTHER PUBLICATIONS

Lewis et al. "A Novel Method for Extracting Respiration Rate and Relative Tidal Volume from Infrared Thermography" Psychophysiology. Jul. 2011 ; 48(7): 877-887 (Year: 2011).*
(Continued)

*Primary Examiner* — Nathan J Jenness
(74) *Attorney, Agent, or Firm* — Revolution IP, PLLC

(57) ABSTRACT

Provided is a respiration analysis system using a gas image detection method, the respiration analysis system including: an exhalation capturing unit provided adjacent to a subject and capturing an image of exhalation exhaled from the mouth and nose of the subject; and a control unit electrically connected to the exhalation capturing unit, and calculating and storing, as data, a respiration cycle and respiration volume from the image captured through the exhalation
(Continued)

capturing unit. Accordingly, provided is the respiration analysis system using the gas image detection method, in which not only respiration of the subject is measured in a non-contact manner, but also hypopnea is determined by quantifying volume of the exhalation exhaled by the subject, thereby inferring a disease caused by the hypopnea.

8 Claims, 4 Drawing Sheets

(51) Int. Cl.

| | | |
|---|---|---|
| *A61B 5/0205* | (2006.01) | |
| *A61B 5/083* | (2006.01) | |
| *A61B 5/091* | (2006.01) | |
| *A61B 5/08* | (2006.01) | |
| *H04N 5/33* | (2006.01) | |
| *A61B 5/291* | (2021.01) | |
| *A61B 5/369* | (2021.01) | |
| *A61B 5/024* | (2006.01) | |

(52) U.S. Cl.
CPC ............ *A61B 5/02055* (2013.01); *A61B 5/08* (2013.01); *A61B 5/291* (2021.01); *A61B 5/369* (2021.01); *A61B 5/6801* (2013.01); *A61B 5/742* (2013.01); *H04N 5/33* (2013.01); *A61B 5/024* (2013.01); *A61B 5/0816* (2013.01); *A61B 5/0836* (2013.01); *A61B 5/091* (2013.01)

(58) Field of Classification Search
CPC ....... A61B 5/6801; A61B 5/742; A61B 5/024; A61B 5/0816; A61B 5/0836; A61B 5/091; A61B 5/0826; A61B 5/1032; A61B 5/0077

See application file for complete search history.

(56) References Cited

U.S. PATENT DOCUMENTS

| | | | |
|---|---|---|---|
| 2012/0289850 A1* | 11/2012 | Xu ................ | A61B 5/015 600/529 |
| 2013/0079658 A1 | 3/2013 | Cardoso et al. | |
| 2013/0245396 A1* | 9/2013 | Berman .............. | G06F 19/3418 600/301 |
| 2016/0262636 A1 | 9/2016 | Min et al. | |
| 2017/0367651 A1* | 12/2017 | Tzvieli ................ | A61B 5/0816 |

FOREIGN PATENT DOCUMENTS

| | | |
|---|---|---|
| KR | 10-2004-0045364 A | 6/2004 |
| KR | 10-1070389 B1 | 10/2011 |
| KR | 10-1242755 B1 | 3/2013 |
| KR | 10-2014-0057867 A | 5/2014 |
| KR | 10-2015-0033197 A | 4/2015 |
| KR | 10-2016-0007512 A | 1/2016 |
| KR | 10-2016-0110847 A | 9/2016 |

OTHER PUBLICATIONS

Cardone et al. "Thermal Infrared Imaging-Based Computational Psychophysiology for Psychometrics" Computational and Mathematical Methods in Medicine. vol. 2015, Article ID 984353, 8 pages (Year: 2015).*

Pereira et al. "Remote monitoring of breathing dynamics using infrared thermography" Biomedical Optics Express Nov. 1, 2015 | vol. 6, No. 11 (Year: 2015).*

Al-Kaldi, Farah, Elphick, Heather, Saatchi, Reza and Burke, Derek (2015). "Respiratory rate measurement in children using a thermal camera." International Journal of Scientific and Engineering Research, 6 (4), 1748-1756 (Year: 2015).*

International Search Report for PCT/KR2017/011018 dated Jan. 17, 2018 from Korean Intellectual Property Office.

* cited by examiner

BREATH ANALYSIS SYSTEM USING GAS IMAGE DETECTION METHOD

TECHNICAL FIELD

The present disclosure relates to a breath analysis system, and more particularly, to a breath analysis system using a gas image detection method, in which an image of exhalation of a subject is captured with a gas image detection infrared camera, respiration is quantified by using the captured image, and respiration of the subject, a respiration volume, and a respiration component are measured by using a quantitative difference of the respiration or a change in a temperature or the like.

BACKGROUND ART

In general, there are many people who snore severely among adults over 30s, and such snoring is caused by extreme fatigue, obesity, stress, rhinitis, and sore throat.

Problems with the snoring are that the snoring may cause an apnea syndrome in which respiration is stopped for several seconds to several tens of seconds, thereby causing a serious fatigue phenomenon that causes a sudden drop in the quality of life to cause deterioration of efficiency of learning and work, and industrial accidents and traffic accidents, and in severe cases, dysfunction in cardiovascular activity and brain activity may be caused due to lack of oxygen supply in the body. In particular, a sleep apnea syndrome may be the cause of sudden death or unexpected death in a patient with heart disease, such as arrhythmia, myocardial infarction, or cardiac failure, or a patient with brain disease, such as cerebral infarction or cerebral apoplexy.

In order to prevent damage from the sleep apnea syndrome, a person with the sleep apnea syndrome may be cautious on his/her own, but unfortunately, it is difficult to self-realize the sleep apnea syndrome.

Thus, although family members of the person could observe whether person has the sleep apnea syndrome, it is not easy to observe the person for a long time without sleeping since the sleep apnea syndrome is considered as a state in which respiration stops 20 times or more during 7 hours of sleep.

Recently, an apparatus for measuring and monitoring such apnea syndrome has been introduced, and there is an apparatus that measures the apnea syndrome by measuring and inputting, to a computer, a change in ventilation volume according to a change of respiration during sleep by mounting a respiration mask suitable to the size of the mouth and nose of a target.

Such a mask is unable to be unified to all people but should be specially manufactured according to shapes of the mouth and nose of the target. Also, an expensive conversion apparatus and software are required to convert the change in the respiration ventilation volume measured for a long time to an electric signal, input the electric signal to the computer, and analyze the electric signal, and the help from a specialist or a medical technician is required.

In addition to a conventional sleep apnea syndrome measuring apparatus being complicated to use and being expensive, since a special mask is worn on the mouth and nose during sleep and a connection line transmitting the respiration ventilation volume is lengthily connected to the computer, the measuring apparatus itself becomes stress, thereby affecting the sleep.

The conventional prior art may be identified in KR 10-2015-0033197 (published on Apr. 2, 2015).

DESCRIPTION OF EMBODIMENTS

Technical Problem

The present disclosure is directed to providing a respiration analysis system using a gas image detection method, in which an image of exhalation of a subject is captured with a gas image detection infrared camera, and not only respiration of the subject may be measured in a non-contact manner by quantifying the respiration by using the captured image, but also a disease caused by hypopnea may be inferred by quantifying volume of exhalation exhaled by the subject to determine the hypopnea.

Solution to Problem

According to an aspect of the present disclosure, a respiration analysis system using a gas image detection method, the respiration analysis system includes: an exhalation capturing unit provided adjacent to a subject and capturing an image of exhalation exhaled from the mouth and nose of the subject; and a control unit electrically connected to the exhalation capturing unit, and calculating and storing, as data, a respiration cycle and respiration volume from the image captured through the exhalation capturing unit.

The exhalation capturing unit may capture a thermogram image in which a color or color density is changed according to changes in a temperature and humidity according to the exhalation exhaled from the mouth and nose of the subject, or capture a thermogram image in which a color or color density is changed according to a distribution of carbon dioxide in the exhalation exhaled from the mouth and nose of the subject, by using an infrared camera.

A plurality of the exhalation capturing units may be provided to capture an image of the exhalation on an orthogonal line based on the face of the subject.

The respiration analysis system may further include a bio-signal measuring unit electrically connected to the control unit to be mounted on the body of the subject and measuring a bio-signal of the subject, wherein the bio-signal measuring unit may include: a brainwave measuring sensor mounted on the head of the subject and measuring brainwaves of the subject; a temperature measuring sensor mounted on the body of the subject and measuring a temperature of the subject; and a pulse measuring sensor mounted on the body of the subject and measuring a pulse of the subject.

The respiration analysis system may further include a display unit electrically connected to the exhalation capturing unit and the control unit, display data according to a bio-signal stored in the control unit, and display the image of exhalation, which is to be captured or is captured.

The exhalation capturing unit, the control unit, and the display unit may be integrated in one body and configured as a wearable device mounted on the head or body of an observer observing the respiration of the subject or as a remote examination device using a computer and a network system.

Advantageous Effects of Disclosure

In a respiration analysis system using a gas image detection method according to the present disclosure, respiration of a subject can be measured in a non-contact manner by capturing a thermogram image of exhalation of the subject by using an infrared camera and quantifying the respiration by using the captured image.

Also, not only the respiration but also hypopnea can be determined by quantifying volume of exhalation exhaled by the subject, and thus a disease caused by the hypopnea can be inferred.

BEST MODE

The present disclosure provides a respiration analysis system using a gas image detection method, the respiration analysis system including: an exhalation capturing unit provided adjacent to a subject and capturing an image of exhalation exhaled from the mouth and nose of the subject; and a control unit electrically connected to the exhalation capturing unit, and calculating and storing, as data, a respiration cycle and respiration volume from the image captured through the exhalation capturing unit. Accordingly, not only respiration of the subject is measured in a non-contact manner, but also hypopnea is determined by quantifying volume of the exhalation exhaled by the subject, thereby inferring a disease caused by the hypopnea.

Mode of the Invention

Hereinafter, the present disclosure will be described more fully with reference to the accompanying drawings, in which exemplary embodiments of the present disclosure are shown. The terms or words used herein must not be interpreted in their common or dictionary definitions, but must be interpreted in the meanings and concept corresponding to the aspect of the present disclosure, based on the principle that the inventor(s) can suitably define the concept of terms in order to describe the present disclosure in the best manner. Accordingly, the embodiments and drawings described herein are only preferred examples, and do not represent the technical aspects of the present disclosure. Thus, one of ordinary skill in the art understands that the present disclosure may be embodied in many different forms.

The present disclosure relates to a respiration analysis system using a gas image detection method, in which an image of exhalation of a subject is captured with a gas image detection infrared camera, respiration is quantified by using the captured image, and respiration of the subject, a respiration volume, and a respiration component are measured by using a quantitative difference of the respiration or a change in a temperature or the like, and will now be described with reference to accompanying drawings.

Figure 1:
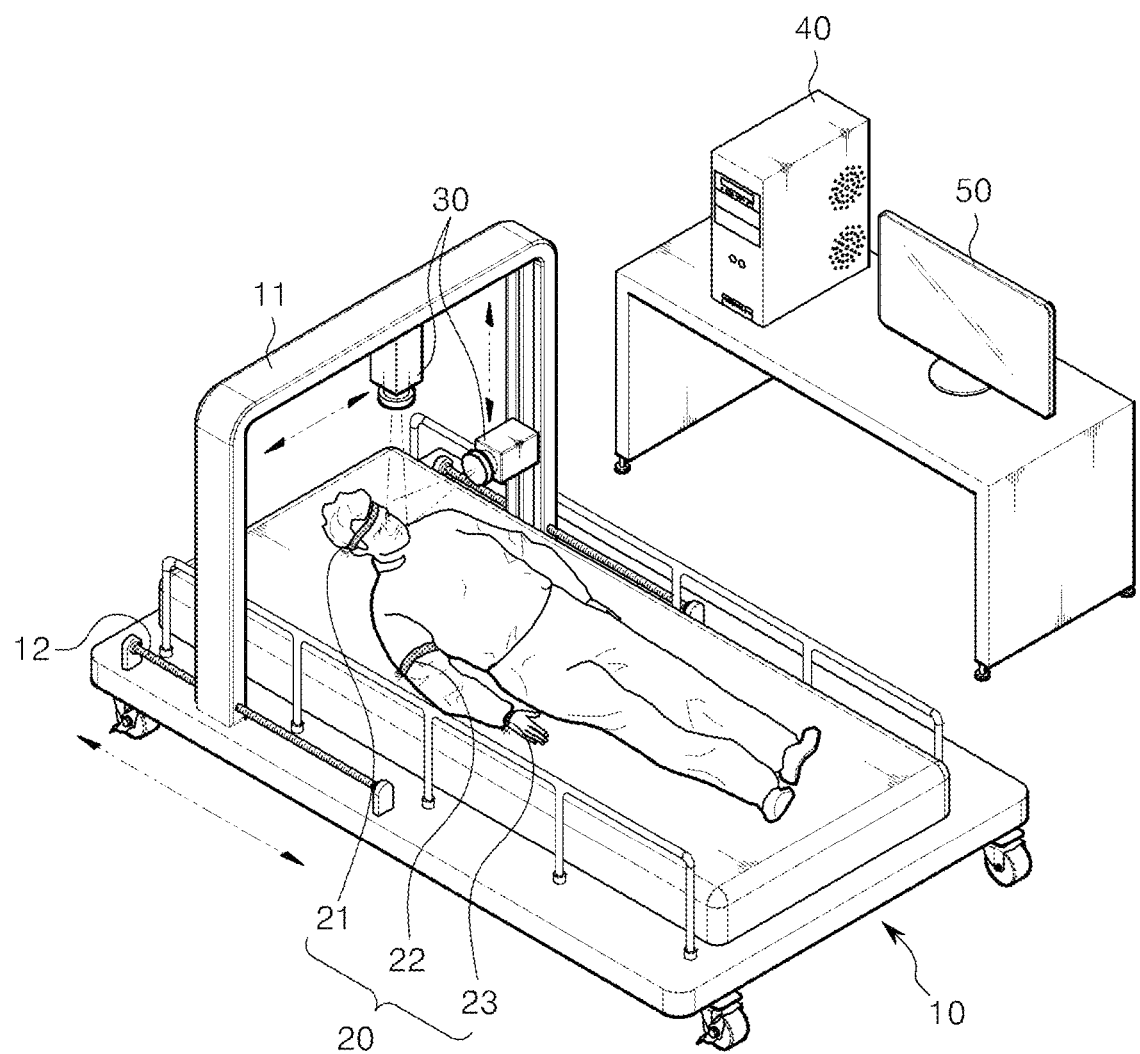
FIG. 1 is a diagram schematically illustrating a respiration analysis system using a gas image detection method, according to an embodiment of the present disclosure.
Figure 2:
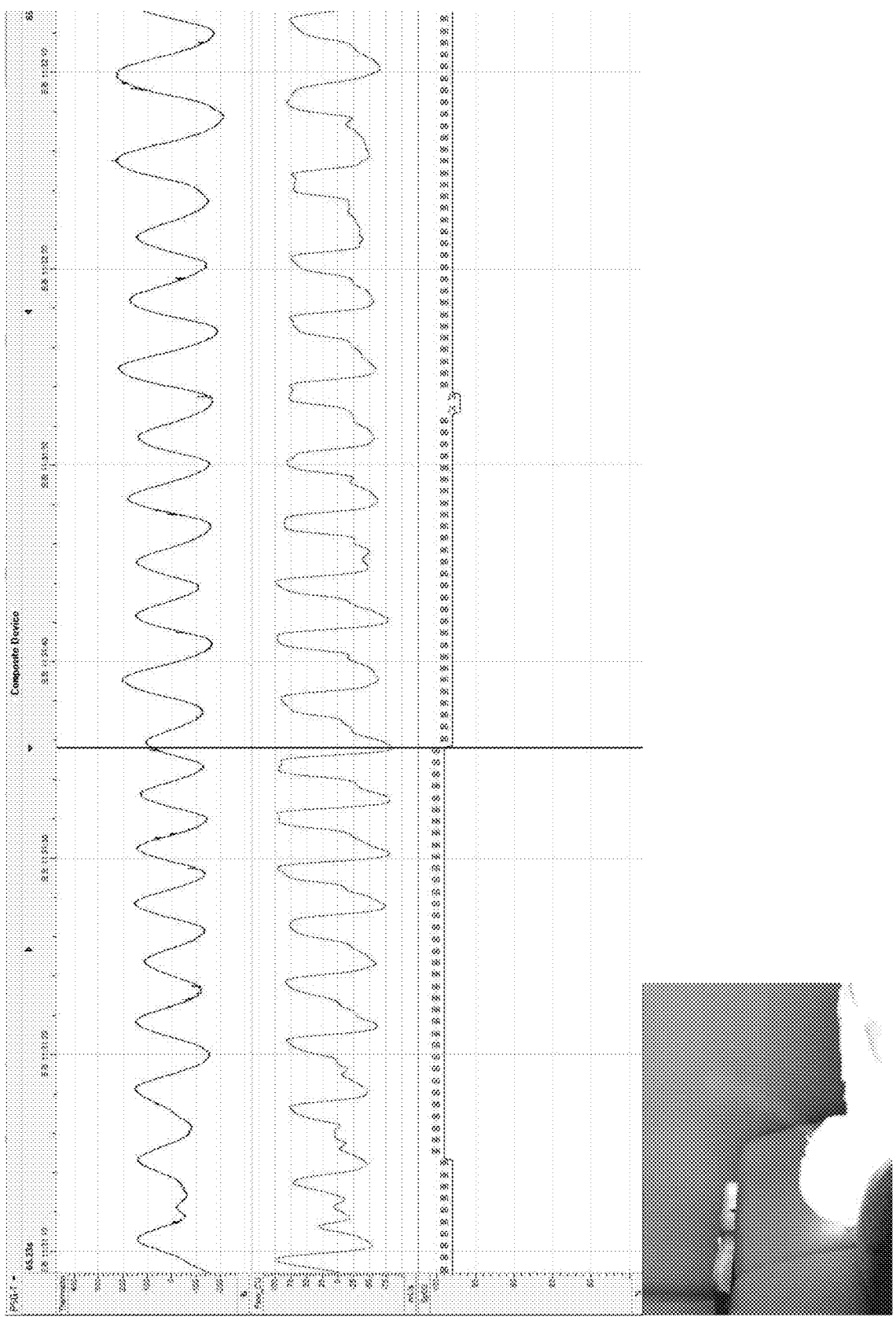
FIG. 2 is an example diagram of an image of normal respiration with an air current of 100% captured by an exhalation capturing unit of the respiration analysis system of FIG. 1, and a graph of a temperature of the respiration, respiration volume, and concentration of carbon dioxide according to time.
Figure 3:
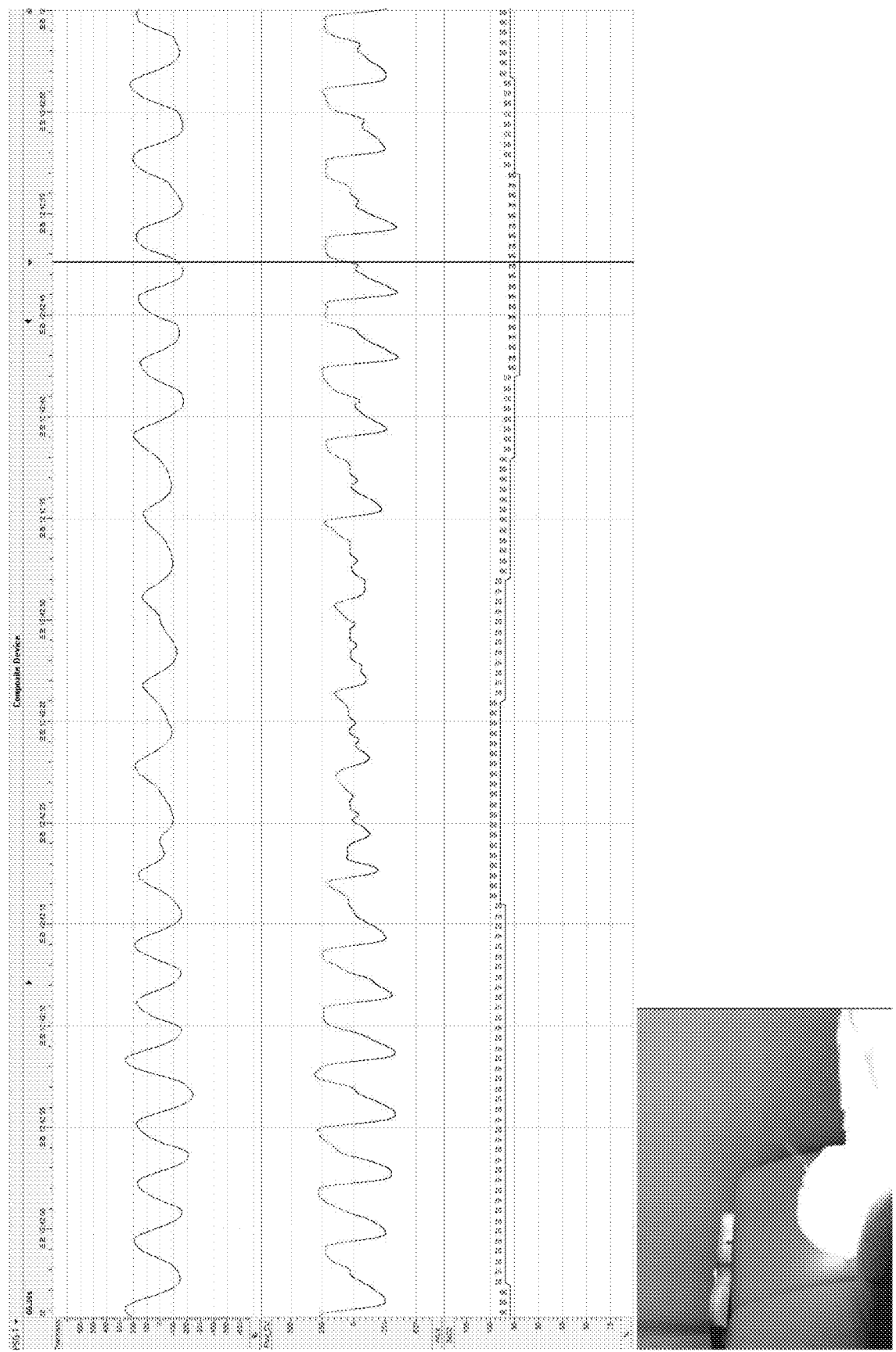
FIG. 3 is an example diagram of an image of air current decreased respiration with an air current of 50% captured by the exhalation capturing unit of the respiration analysis system of FIG. 1, and a graph of a temperature of the respiration, respiration volume, and concentration of carbon dioxide according to time.
Figure 4:
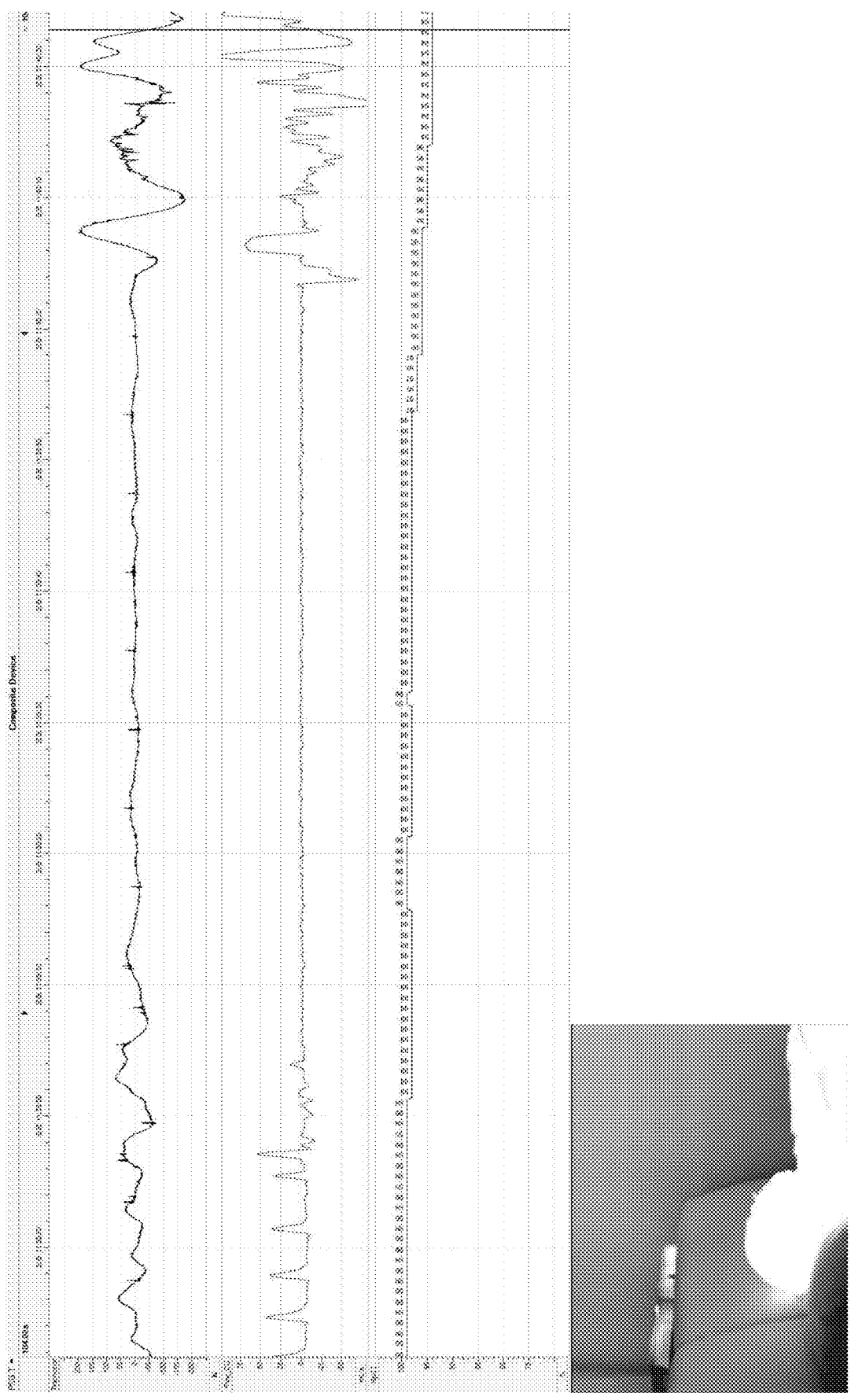
FIG. 4 is an example diagram of an image of air current lost respiration with an air current of 0% captured by the exhalation capturing unit of the respiration analysis system of FIG. 1, and a graph of a temperature of the respiration, respiration volume, and concentration of carbon dioxide according to time.

FIG. 1 is a diagram schematically illustrating a respiration analysis system using a gas image detection method, according to an embodiment of the present disclosure, FIG. 2 is an example diagram of an image of normal respiration with an air current of 100% captured by an exhalation capturing unit of the respiration analysis system of FIG. 1, and a graph of a temperature of the respiration, respiration volume, and concentration of carbon dioxide according to time, FIG. 3 is an example diagram of an image of air current decreased respiration with an air current of 50% captured by the exhalation capturing unit of the respiration analysis system of FIG. 1, and a graph of a temperature of the respiration, respiration volume, and concentration of carbon dioxide according to time, and FIG. 4 is an example diagram of an image of air current lost respiration with an air current of 0% captured by the exhalation capturing unit of the respiration analysis system of FIG. 1, and a graph of a temperature of the respiration, respiration volume, and concentration of carbon dioxide according to time.

Referring to FIG. 1, the respiration analysis system using the gas image detection method, according to an embodiment of the present disclosure includes an exhalation capturing unit 30 and a control unit 40, and in addition, may further include a measuring bed 10, a bio-signal measuring unit 20, and a display unit 50.

First, referring to the exhalation capturing unit 30 according to an embodiment of the present disclosure in detail, as shown in FIG. 1, the exhalation capturing unit 30 is provided around the face of the subject to capture an image of exhalation exhaled from the mouth and nose of the subject.

Here, the exhalation capturing unit 30 may capture a thermogram image in which a color or color density around the mouth and nose of the subject is changed according to changes in a temperature and humidity according to the exhalation exhaled from the mouth and nose of the subject, or capture a thermogram image in which a color or color density around the mouth and nose of the subject is changed according to a distribution of carbon dioxide in the exhalation exhaled from the mouth and nose of the subject, by using an infrared camera, as shown in FIGS. 2 and 3.

The thermogram image captured by using the infrared camera denotes an image in which a temperature distribution of a certain surface obtained via measurement of infrared rays emitted from the certain surface is displayed in light and shade of black and white or in colors, and the exhalation capturing unit 30 according to an embodiment of the present disclosure may capture the thermogram image of the changes in temperature and humidity according to the exhalation around the mouth and nose of the subject, via the infrared rays emitted from the exhalation exhaled from the mouth and nose of the subject.

In addition, the thermogram image of the distribution of carbon dioxide that is a selected gas in the exhalation exhaled from the mouth and nose of the subject may be captured via infrared filtering of a certain frequency band.

Also, a plurality of the exhalation capturing units 30 may be provided on a holder 11 to capture an image of the exhalation on an orthogonal line based on the face of the subject, and according to an embodiment of the present disclosure of FIG. 1, the exhalation capturing unit 30 may be provided on each of the front and side of the face of the subject to capture the image of the exhalation exhaled from the mouth and nose of the subject from each of the front and side of the face of the subject.

At this time, the exhalation capturing unit 30 may track and move along the face of the subject, along a length direction.

The exhalation capturing unit 30 described above is electrically connected to the control unit 40 and transmits the captured thermogram image to the control unit 40, and the control unit 40 is capable of data communication by being electrically connected to the exhalation capturing unit 30 and processes and stores the thermogram image while receiving the image captured by the exhalation capturing unit 30.

Here, the control unit 40 processes the thermogram image that is the image captured through the exhalation capturing unit 30 such that the respiration is quantified, and at this time, to quantify the respiration, the control unit 40 divides the captured thermogram image according to frames, selects a region around the nose and mouth of the subject as a measurement region from each frame, virtually divides the selected measurement region into lattices of respective sizes as a criterion of the measurement region, counts the number of lattices whose color is changed according to the respiration of the subject in the measurement region divided into the plurality of lattices, calculates a color density changed degree of the lattices whose color is changed, and stores the color density changed degree as data according to time.

Accordingly, the respiration may be determined based on the color change around the mouth and nose of the subject via the thermogram image, and the respiration may be quantified because the respiration volume may be determined based on the number of lattices whose color is changed and on the color density.

When the respiration is quantified via the above processes, the subject is able to compare the respiration, a respiration cycle, and the respiration volume based on the data, and thus the apnea of the subject may be inferred.

In addition, the measuring bed 10 may include a base provided on the ground, such as a general bed, and a mattress provided on the base and on which the subject lies.

Also, the holder 11 holding the exhalation capturing unit 30 is provided at the measuring bed 10, wherein the holder 11 is located at a head position of the subject at the measuring bed 10 such that the exhalation capturing unit 30 is located around the face of the subject.

Here, the holder 11 may be moved by a moving unit 12 provided at the measuring bed 10 such that the face of the subject is traced and photographed at the measuring bed 10.

Here, regarding the moving of the holder 11, an operator may manually move the holder 11 and the exhalation capturing unit 30 by directly manipulating a manipulating unit, such as a joystick or the like, or the holder 11 and the exhalation capturing unit 30 may automatically move by tracking the face of the subject according to location coordinates displacement of the face of the subject extracted based on the image captured by the exhalation capturing unit 30.

A moving screw may be used as the moving unit 12 moving the holder 11, and a linear motor or the like may be used for the exhalation capturing unit 30 moving along a length direction of the holder 11, but the present disclosure is not limited thereto.

Also, the bio-signal measuring unit 20 may be mounted on the body of the subject and measure the bio-signal of the subject.

Here, the bio-signal measuring unit 20 may include a brainwave measuring sensor 21 mounted on the head of the subject and measuring brainwaves of the subject, a temperature measuring sensor 22 mounted on the body of the subject and measuring the temperature of the subject, and a pulse measuring sensor 23 mounted on the body of the subject and measuring a pulse of the subject. At least one type of the above measuring sensors may be mounted on the body of the subject as occasion demands, and a measurement value thereof may be transmitted to the control unit 40.

The bio-signal of the subject measured by the bio-signal measuring unit 20 according to an embodiment of the present disclosure is transmitted to the control unit 40 that is electrically connected to the bio-signal measuring unit 20 to enable data communication.

Also, the bio-signal measuring unit 20 according to an embodiment of the present disclosure is described limitedly to the brainwave measuring sensor 21, the temperature measuring sensor 22, and the pulse measuring sensor 23, but is not limited thereto, and may further include an electrocardiogram (ECG) measuring sensor for measuring a cycle and degree of heartbeats.

Also, the display unit 50 according to an embodiment of the present disclosure is electrically connected to the exhalation capturing unit 30 and the control unit 40, displays data of the bio-signal stored in the control unit 40, and displays the captured image of the exhalation.

FIGS. 2 through 4 illustrate images of respiration of air currents of 100%, 50%, and 0% captured by an exhalation capturing unit of a respiration analysis system according to an embodiment of the present disclosure, and graphs of a temperature, respiration volume, and concentration of carbon dioxide of the respiration according to time. An image of exhalation of a subject may be captured by a gas image detection infrared camera, respiration may be quantified by using the captured image, and a disease related to the respiration may be inferred based on quantified data.

A respiration analysis system using a gas image detection method, according to an embodiment of the present disclosure is not only used to diagnose snoring or sleep apnea, but to monitor respiration and respiration volume of a risk group, such as an infant, a critical patient, or an aged citizen, as well as a normal person, and is able to measure a respiration change of a subject without the subject having to wear a separate device not only when the subject is sleeping, but also when the subject is awake.

In addition, it is possible to measure the number of breathings and a respiration cycle, distinguish breathing and coughing, and measure a coughing degree, according to existence of respiration, quantification of respiration, and shape and speed of an air current, and it is also possible to diagnose a disease by medically analysing a respiration component of a person. For example, nitric oxide (NO) in the exhalation (expiration) of a person is increased due to a respiratory infection, such as asthma, and thus by measuring NO, a respiratory disease (cold, asthma, or the like) may be screened.

As such, a respiratory disease may be diagnosed in a non-contact manner, and by mounting a miniature infrared camera to a smart phone or using an infrared camera mounted on a personal computer (PC), a patient may be examined and analyzed in real-time for remote medical diagnosis.

Also, a respiration analysis system using a gas image detection method, according to an embodiment of the present disclosure may measure a gas of different components according to a wavelength of infrared rays used in a camera, and for example, an alcohol component in respiration is measured by using a camera of a wavelength capable of measuring ethanol, and thus drunk driving may be indirectly determined by determining drinking in a non-contact manner.

Also, a respiration analysis system using a gas image detection method, according to an embodiment of the present disclosure may be configured as a wearable device, such as a head-mounted display (HMD) or Google glass, in which an exhalation capturing unit capturing an image of exhalation of a subject, a control unit calculating and storing, as data, a respiration cycle and respiration volume by using the captured image, and a display unit displaying data according to a bio-signal and displaying the image of exhalation that is to be captured or is captured are integrated as one body, thereby enabling not only non-contact medical diagnosis, but also remote medical diagnosis using a communication unit.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

The invention claimed is:

1. A respiration analysis system using a gas image detection method, the respiration analysis system comprising:
    an exhalation capturing unit configured to be provided adjacent to a subject and capture an image of exhalation exhaled from the mouth and nose of the subject;
    a measuring bed comprising a base provided on the ground and a mattress provided on the base;
    a holder configured to hold the exhalation capturing unit and be provided at the measuring bed, wherein the holder is configured to be moved by a moving unit provided at the measuring bed such that the subject is traced and photographed on the measuring bed; and
    a control unit electrically connected to the exhalation capturing unit and configured to calculate and store, as data, a respiration cycle and respiration volume from the image captured through the exhalation capturing unit, wherein the control unit is configured to
        divide the image captured by the exhalation capturing unit according to frames,
        select a measurement region from each frame,
        virtually divide the selected measurement region into lattices of respective sizes as a criterion of the measurement region,
        count the number of lattices whose color is changed according to the respiration of the subject in the measurement region divided into the plurality of lattices,
        calculate a color density changed degree of the lattices whose color is changed,
        store the color density changed degree as the data according to time, and
        determine the respiration cycle and respiration volume based on the number of lattices whose color is changed and on the color density.

2. The respiration analysis system of claim 1, wherein the exhalation capturing unit captures a thermogram image in which a color or color density is changed according to changes in a temperature and humidity according to the exhalation exhaled from the mouth and nose of the subject, by using an infrared camera.

3. The respiration analysis system of claim 1, wherein the exhalation capturing unit captures a thermogram image in which a color or color density is changed according to a distribution of carbon dioxide in the exhalation exhaled from the mouth and nose of the subject, by using an infrared camera.

4. The respiration analysis system of claim 2, wherein a plurality of the exhalation capturing units are provided to capture an image of the exhalation on an orthogonal line based on the face of the subject.

5. The respiration analysis system of claim 3, wherein a plurality of the exhalation capturing units are provided to capture an image of the exhalation on an orthogonal line based on the face of the subject.

6. The respiration analysis system of claim 1, further comprising a bio-signal measuring unit electrically connected to the control unit to be mounted on the body of the subject and measuring a bio-signal of the subject.

7. The respiration analysis system of claim 6, wherein the bio-signal measuring unit comprises:
    a brainwave measuring sensor configured to measure brainwaves of the subject;
    a temperature measuring sensor configured to measure a temperature of the subject; and
    a pulse measuring sensor configured to measure a pulse of the subject.

8. The respiration analysis system of claim 1, further comprising a display unit electrically connected to the exhalation capturing unit and the control unit, wherein the display unit is configured to display the data according to a bio-signal stored in the control unit, and display the captured image of exhalation.

* * * * *